(12) United States Patent
Berberich

(10) Patent No.: US 8,114,094 B2
(45) Date of Patent: Feb. 14, 2012

(54) DEVICE FOR INTRODUCING AN ANCHOR ELEMENT INTO A BONE

(75) Inventor: Sascha Berberich, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 290 days.

(21) Appl. No.: 11/962,358

(22) Filed: Dec. 21, 2007

(65) Prior Publication Data

US 2008/0154313 A1    Jun. 26, 2008

(30) Foreign Application Priority Data

Dec. 21, 2006   (DE) .......................... 10 2006 062 401

(51) Int. Cl.
*A61B 17/58* (2006.01)
*A61B 17/60* (2006.01)
*A61F 2/00* (2006.01)

(52) U.S. Cl. ........................ 606/104; 606/232; 606/60

(58) Field of Classification Search .............. 606/60, 606/86 R, 148, 232, 228, 916, 104
See application file for complete search history.

(56) References Cited

U.S. PATENT DOCUMENTS

| | | | | |
|---|---|---|---|---|
| 5,690,676 | A | * | 11/1997 | DiPoto et al. .................. 606/232 |
| 5,868,789 | A | * | 2/1999 | Huebner .......................... 606/232 |
| 5,957,924 | A | * | 9/1999 | Tormala et al. ................. 606/139 |
| 7,320,701 | B2 | * | 1/2008 | Haut et al. ...................... 606/232 |
| 2004/0243179 | A1 | * | 12/2004 | Foerster .......................... 606/232 |
| 2006/0253119 | A1 | * | 11/2006 | Berberich et al. ............... 606/72 |

FOREIGN PATENT DOCUMENTS

| | | |
|---|---|---|
| DE | 202 17 422 | 2/2003 |
| EP | 1 484 022 | 8/2004 |
| WO | 2004/062507 | 7/2004 |

OTHER PUBLICATIONS

Company catalog produced by Karl Storz GmbH & Co. KG, Tuttlingen, "Storz, Die Welt Der Endoskopie, Arthroskopie, Sportmedizin, Wirbelsäulenchirurgie" [Storz, The World of Endoscopy, Arthroscopy, Sports Medicine and Spinal Surgery], 2nd editions Jan. 2005, p. 114 (equipment No. 28179 TI), 4 pages.

* cited by examiner

*Primary Examiner* — Thomas C. Barrett
*Assistant Examiner* — Christine Nelson
(74) *Attorney, Agent, or Firm* — St. Onge Steward Johnston & Reens LLC

(57) ABSTRACT

A device for introducing an anchor element into a bone, having a loop of thread extending laterally from said anchor element. The device has an elongate body having a distal end which can be inserted into the anchor element in a rotationally locked manner. A distal end portion of said elongate body has at least one cutting for inserting the loop protruding laterally from the anchor element. The cutting is designed in such a way that the loop when inserted into the cutting is prevented from falling laterally away. The elongate body further has a longitudainlly extending recess in an area of the cutting. The recess is designed as an opening extending right through the elongate body, such that the loop inserted into the cutting can be gripped from the outside.

13 Claims, 7 Drawing Sheets

DEVICE FOR INTRODUCING AN ANCHOR ELEMENT INTO A BONE

BACKGROUND OF THE INVENTION

The invention relates to a device for introducing an anchor element, in which a thread is engaged, into a bone in order to fix a tissue that is detached from the bone, with an elongate body whose distal end is designed in such a way that it can be connected to the anchor element in a rotationally locked manner.

A device used for introducing an anchor element, and having these structural features, is known from the company catalog produced by Karl Storz GmbH & Co. K G, Tuttlingen, "STORZ, DIE WELT DER ENDOSKOPIE, ARTHROSKOPIE, SPORT-MEDIZIN, WIRBELSÄULENCHIRURGIE" [STORZ, THE WORLD OF ENDOSCOPY, ARTHROSCOPY, SPORTS MEDICINE AND SPINAL SURGERY], 2nd edition January 2005, page 114 (equipment No. 28179 TI).

Such devices are used to introduce an anchor element, in which a thread is engaged, into a bone, such that the anchor element is anchored in the bone. Both ends of the thread engaged in the anchor element are tied to a torn tendon or a torn ligament, in order to fix these once again to the bone. A main area of application of such anchor elements is in the fixing of torn tendons in the shoulder region.

The device mentioned at the outset comprises an elongate body, which has a grip arranged at its proximal end. A distal end of the body is provided with a projection that can be introduced into an opening in the anchor element. The distal projection is designed in such a way that the device can be connected to the anchor element in a rotationally locked manner. The device known from the Storz catalog also comprises a lateral binding device for the thread that is threaded through the anchor element. For driving the anchor element into the bone, the two ends of the thread threaded through the anchor element are guided along the body and then wound round the radially protruding binding device.

The introduction of the anchor element into the bone by means of the abovementioned device can be done by two procedures, depending on which anchor element is used.

In the first procedure, a channel is drilled in the bone, and an anchor element is introduced into this drilled channel. For this purpose, the anchor element is fitted onto the distal projection of the device and turned into the bore. After the anchor element is in place, the device is removed, and the tendon is fixed to the bone with the thread ends. To ensure that the anchor element anchors itself in the bore, hook-like or barb-like projections are present on its outer face.

In a second procedure, the tip of the projection of the device extends beyond the distal end of the anchor element, the outer face of which is provided with a screwthread. By impaction and then a rotation movement of the device connected to the anchor element in a rotationally locked manner, the anchor element can dig into the bone and thereby be anchored. Thus, an anchor element of this kind can be fitted without first preparing a bore.

Irrespective of which type of anchor element is used, the ends of the thread threaded through the anchor element, which ends are wound up on the lateral binding device during introduction of the anchor element into the bone, are released from the binding device after the anchor element is inserted into the bone. Before the torn tendon is tied to the two ends of the thread, the two thread ends have to be separated arthroscopically one after the other, which is extremely complicated and requires a great deal of skill, even on the part of an experienced surgeon.

An operating technique has now been developed in which the thread is passed from one side through the transverse opening in the anchor, is curved on the other side to form a loop, and is guided back again in the opposite direction through the transverse bore.

Thus, a loop of the thread protrudes from one side of the anchor element, and two free thread ends on the opposite side.

When the device mentioned at the outset was used with such a thread configuration in the anchor element, difficulties arose in fixing the loop to the screwing-in device.

European patent application EP 1 484 022 A2 discloses an insertion tool for inserting a plurality of suture anchors having at least one locking wing extending radially from the shaft of the anchor. The insertion tool includes an S-shaped slot configured to permit the insertion tool to insert a plurality of suture anchors. The S-shaped slot includes a distal portion appropriately dimensioned for loosely receiving a radially extending wing of suture anchor. An angularly offset proximal portion is configured to receive suture threads, a proximal portion forming a suture guide hub.

International patent application WO 2004/062507 A2 discloses a device for introducing an anchor element having an elongated body whose distal end is designed in such a way that it can be connected to the anchor element in a rotationally locked manner. Within the distal end which is inserted into the hollow body of the anchor element there is provided a gap for receiving a loop of the thread located within the anchor element.

It is an object of the invention to develop a device of the type mentioned at the outset, for introducing an anchor element into a bone, in such a way that, together with a simple construction, the thread is held securely during introduction and can be easily separated thereafter.

SUMMARY OF THE INVENTION

According to the invention, the object is achieved by a device for introducing an anchor element, in which a thread is engaged, into a bone, in order to fix a tissue that is detached from the bone, a loop of said thread extending laterally from said anchor element, said device comprises an elongate body having a distal end which can be inserted into said anchor element in a rotationally locked manner. A distal end portion of said elongate body has at least one cutting for inserting said laterally protruding loop of said anchor element, said cutting being designed in such a way that said loop, when inserted into said cutting, is prevented from falling laterally away from said elongate body. Further said elongate body has a longitudinally extending recess which is present in an area of said cutting, said recess being designed as an opening extending right through said elongate body, such that said loop, inserted into said cutting, can be gripped from the outside.

These measures have the advantage that the loop can be inserted in the cutting after the device has been applied to the anchor element. By pulling on the free ends, the loop is held taut in the cutting. After the free ends have been secured, the loop is held captive on the device.

The anchor element is then introduced into the bone by means of the device according to the invention, using one of the procedures described above. After the anchor element has been fitted into the bone and the free ends have been released, the loop of the thread can be moved back out of the cutting.

The loop inserted in the cutting lies free in the area of the recess and can therefore be very easily gripped by the operating surgeon.

By virtue of the fact that the recess extends in the longitudinal direction of the body, that is to say transversely with respect to the cutting designed as an incision and also with respect to the thread portion of the loop inserted in the cutting, the thread portion can be easily gripped from the outside by an instrument whose distal end is hook-shaped, for example.

The design of the recess as a through-opening has the advantage that the loop can be taken hold of particularly easily. An instrument for gripping the loop can first be guided through the recess, and the hook can be brought into position behind the loop in order then to draw the latter forward. This can be done from both sides of the device.

In another embodiment of the invention, the cutting is designed as an incision extending transversely with respect to a longitudinal axis of the body.

This measure has the advantage that the loop of the thread placed in the incision thus formed slides radially into the incision when the free ends of the thread are drawn tight, and thus sits firmly in the incision. The loop of the tensioned thread is thereby prevented from falling out to the side during introduction of the anchor element into the bone.

In another embodiment, the cutting, seen from proximal to distal, extends with an inclination in the distal direction.

This oblique, inclined profile ensures that the loop is guided radially inward and distally and is secured particularly safely against falling out to the side from the device.

In another embodiment of the invention, the inclination is 30° to approximately 90°, preferably approximately 45°.

A sufficiently steep inclination of the cutting ensures that the thread loop placed in the cutting is prevented from falling out to the side even when the thread tensioning is loosened.

In another embodiment of the invention, the cutting extends around a part of the circumference of the body, preferably around half the circumference.

This measure has the advantage that a cutting designed in this way provides the inserted loop of the thread with a suitably large contact surface. This contributes to a more secure hold of the thread, even when the thread tensioning is loosened.

In another embodiment of the invention, the cutting, seen in the radial direction, has a depth that corresponds at most to half the diameter of the body.

In such a configuration of the device according to the invention, the radially deep insertion has the effect, on the one hand, that the thread loop is held in the cutting in a manner particularly secure against falling out to the side. On the other hand, such a configuration of the cutting ensures that, even with a small diameter, the device has the necessary stability for introducing the anchor element into the bone, which is associated with quite a considerable force being applied to the device.

In another embodiment, the cutting is designed as a slit.

This measure has the advantage that the slit is easy to produce.

In further embodiments of the invention, the recess and the cutting intersect, and the recess intersects the cutting in particular centrally.

These measures have the advantage that the loop inserted in the cutting can be gripped by an instrument from both sides and from upside or downside of the cutting.

It will be appreciated that: the aforementioned features and those still to be explained below can be used not only in the cited combination, but also in other combinations or singly, without departing from the scope of the present invention.

BRIEF DESCRIPTION OF THE DRAWINGS

The invention is described and explained in more detail below on the basis of a selected illustrative embodiment and with reference to the attached drawings, in which.

DETAILED DESCRIPTION OF PREFERRED EMBODIMENTS

Figure 1:
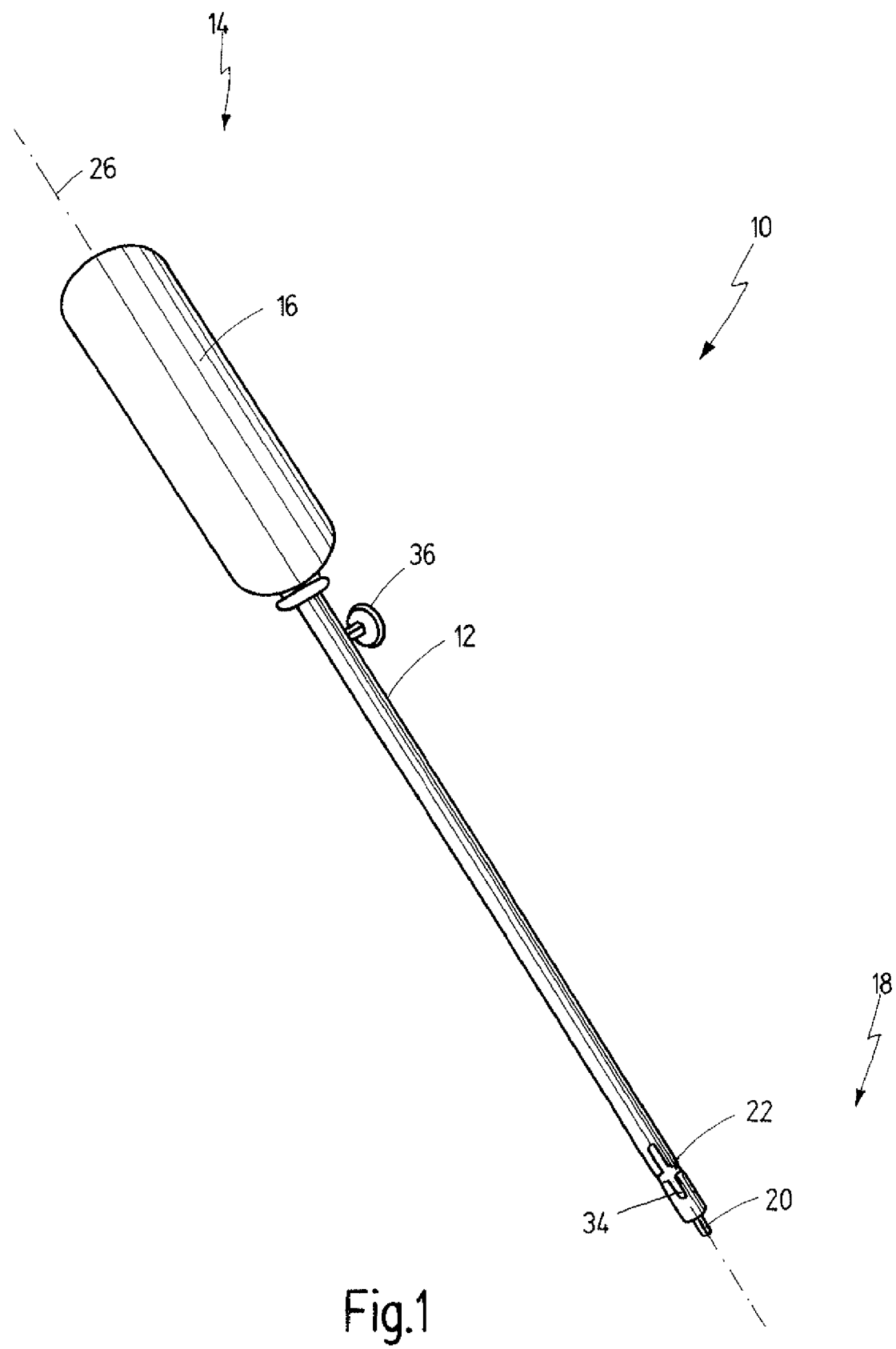
FIG. 1 shows a perspective side view of a device according to the invention.
Figure 2:
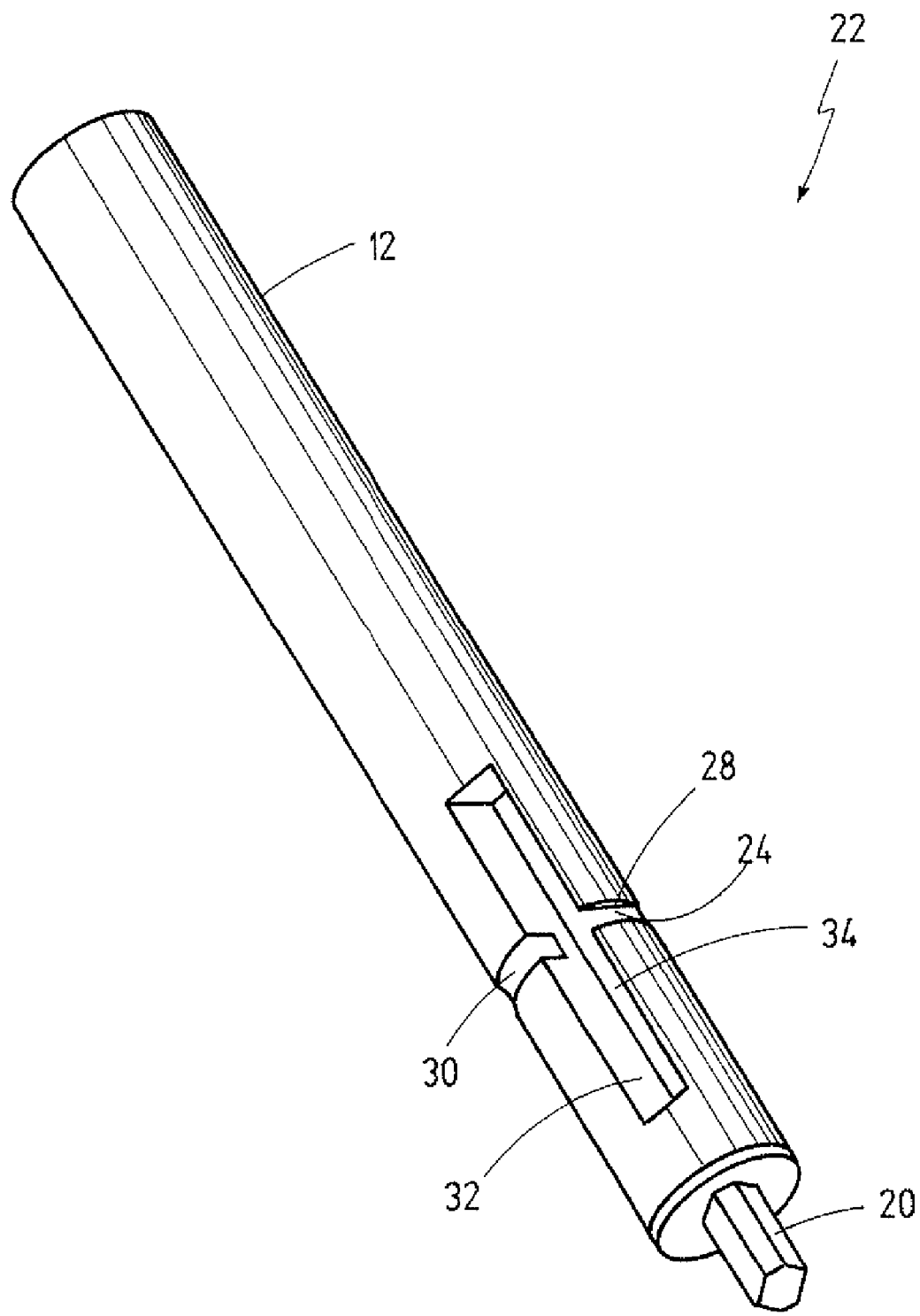
FIG. 2 shows a perspective enlarged side view of a distal end portion of the device according to the invention from FIG. 1.
Figure 3:
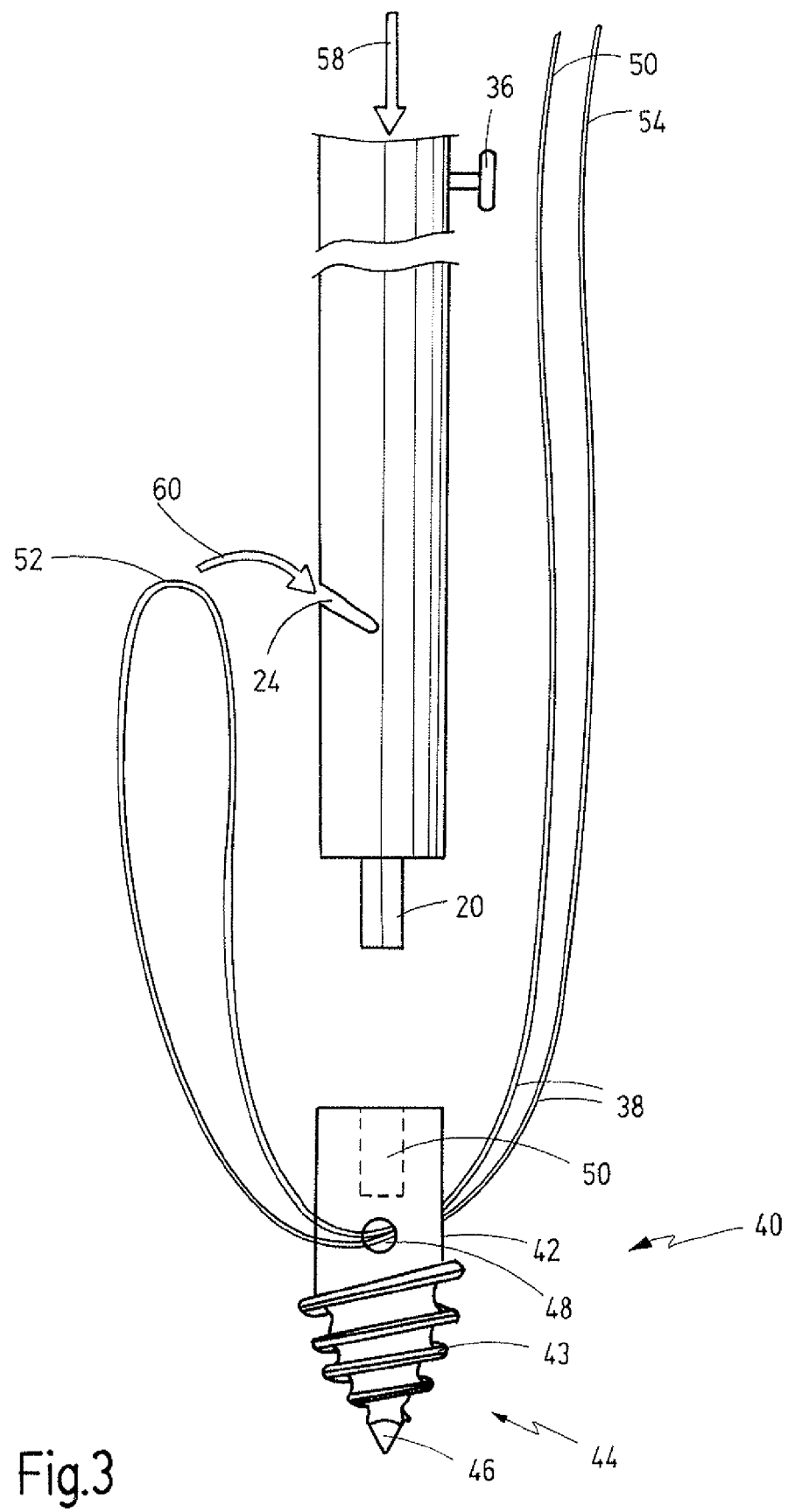
FIG. 3 shows a side view of the distal end portion of the device from FIG. 2, the device being turned through 90° about a longitudinal axis of the device, and also an anchor element through which a thread with a loop is threaded, said anchor element not yet being connected to the device.

A device shown in FIGS. 1 to 3 for introducing an anchor element into a bone is designated in its entirety by reference number 10.

The device 10 according to the invention has an elongate body 12, preferably made of metal. A grip 16 is arranged on a proximal end 14 of the body 12.

A distal end 18 of the body 12 is provided with a projection 20, as can be seen in particular from the enlarged view in FIG. 2. An anchor element (not shown here) can be fitted onto the projection 20 in such a way that the anchor element and the device 10 are connected in a rotationally locked manner. In this illustrative embodiment, the projection 20 has a hexagonal cross section. However, it can also have a different cross section, depending on the configuration of an opening in the anchor element to which the device 10 is to be connected in a rotationally locked manner.

A distal end portion 22 of the body 12 is provided with a cutting 24.

The cutting 24 is designed as an incision 28 extending transversely with respect to a longitudinal axis 26 of the body 12. The cutting 24 extends around the circumference of the body 12. In this illustrative embodiment shown in FIG. 2, it extends around half the circumference.

The cutting 24 is designed as a slit 30, which can easily be produced in the metal body 12 by milling out.

The cutting 24 designed as slit 30 has, seen in the radial direction, a depth that corresponds at most to half the diameter of the body 12, as can be seen from the view in FIG. 2 and in particular from FIG. 3.

Seen from proximal to distal, the cutting 24 is inclined in the distal direction from a cross-sectional surface, for example in the range of 30° to approximately 90°. In the illustrative embodiment shown, the cutting 24 has an inclination of 45°, as can be seen from the view in FIG. 3.

A recess 32 is additionally present in the distal end portion 22, as can be seen from the enlarged view in FIG. 2. The recess 32 extends in the longitudinal direction of the body 12 and is designed as a longitudinally extending groove. The recess 32 is designed as an opening 34 that extends right through the body 12.

FIG. 3 is a side view of the distal end portion 22 of the device 10 according to the invention, this view being turned through 90° about the longitudinal axis 26 compared to the view in FIG. 2.

In this view, a peg 36 can be seen, which protrudes radially from the body 12. The peg 36 is used for fixing the free ends 54, 56 of a thread 38 during introduction of an anchor element 40 into the bone.

FIG. 3 also shows an anchor element 40, which can be fitted onto the projection 20 of the device 10 according to the invention.

The anchor element 40 has a body 42 that narrows at the distal end. Centrally in the body 42, an axial depression 50 is formed which starts from the proximal end and serves to receive the distal projection 20 of tire device 10. The axial depression 50 has a hexagonal cross section that corresponds to the hexagonal shape of the projection 20.

An outer face of the body 42 is provided with a thread 43, which extends approximately from the centre of the body 42 as far as a distal end 44 of the body 42. The distal end 44 is designed as a point 46 in this illustrative embodiment.

In the central area of the body 42 of the anchor element 40, a transverse bore 48 passes through the latter and allows the thread 38 to be threaded through the body 42 of the anchor element 40, as is shown in FIG. 3. The thread 38 is threaded twice through the transverse bore 48, such that a loop 52 of the thread 38 protrudes from one side of the transverse bore 48, whereas two thread ends 54, 56 of the thread 38 protrude from the other side of the transverse bore 48.

Before the anchor element 40 is introduced into a bone, the device 10 is connected to the anchor element 40, by means of the projection 20 of the device 10 being inserted into the axial depression 50 in the anchor element 40. The direction of insertion is indicated by an arrow 58.

The loop 52 of the thread 38 threaded through the transverse bore 48 is then inserted into the cutting 24 designed as slit 30, as is indicated by an arrow 60. The thread ends 54, 56 are then pulled, such that the loop is drawn taut in the slit 30, and the thread ends 54, 56 are then wound onto the peg 36, as is shown in FIG. 4.

Figure 4:
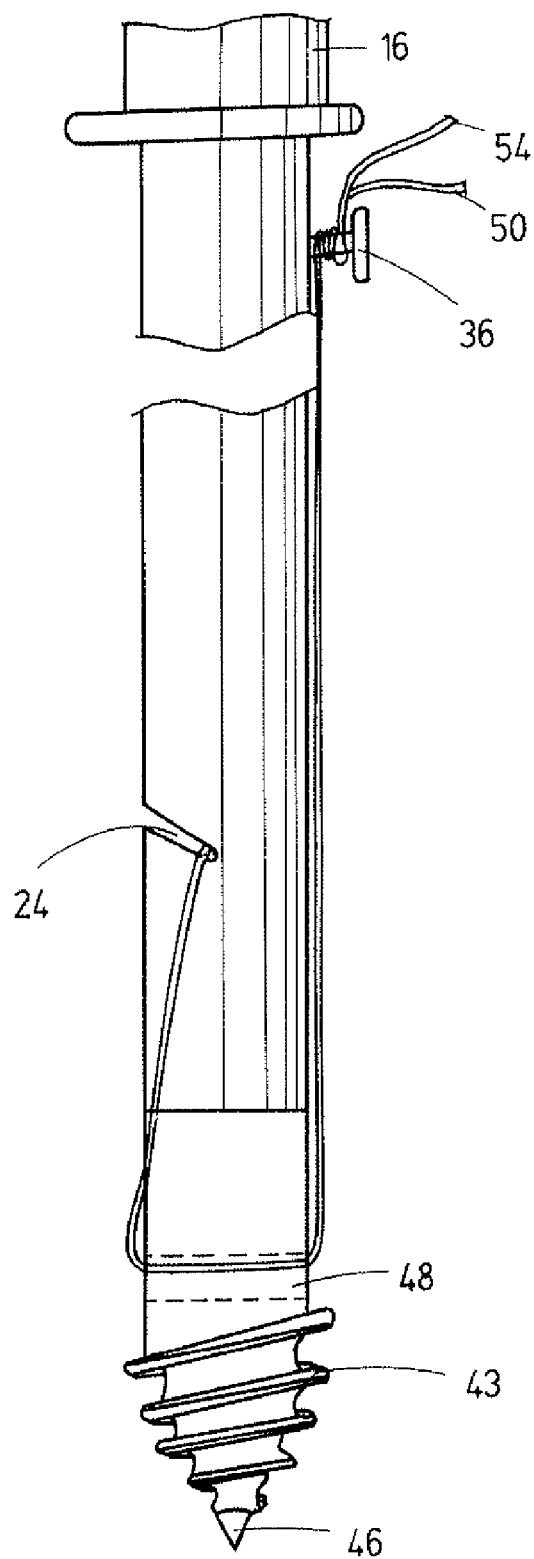
FIG. 4 shows a side view of a distal end portion of an assembly composed of the anchor element and of the device from FIG. 3, a loop of the thread threaded through the anchor element being inserted into a cutting of the device.
Figure 5:
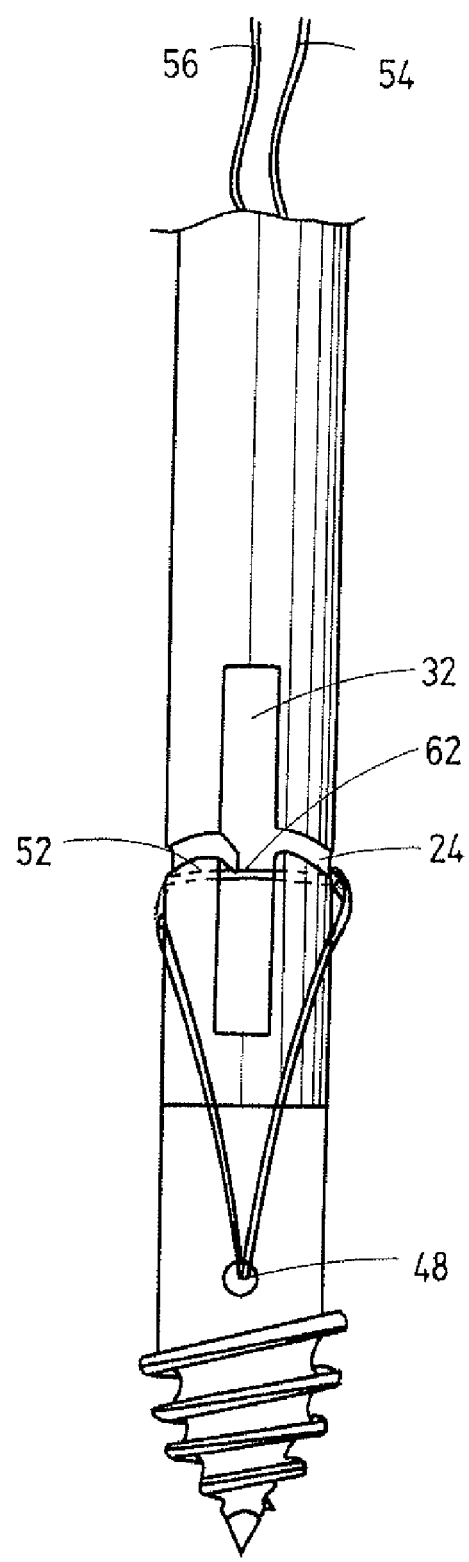
FIG. 5 shows a view comparable to that of FIG. 4, but turned through 90° about the longitudinal axis of the device.

FIG. 5 shows the assembly composed of the anchor element 40 and the device 10, the assembly having been turned through 90° about the longitudinal axis 26 compared to the view in FIG. 4.

As will be seen from this view, the recess 32 and the cutting 24 intersect centrally. By means of such a configuration of the device according to the invention, a thread portion 62 of the thread 38 threaded through the anchor element 48, specifically of the loop 52 inserted in the cutting 24, lies free and can be easily gripped from the outside. The fact that the recess 32 and the cutting 24 intersect centrally means that the thread portion 62 can be gripped from above or from below.

Figure 6:
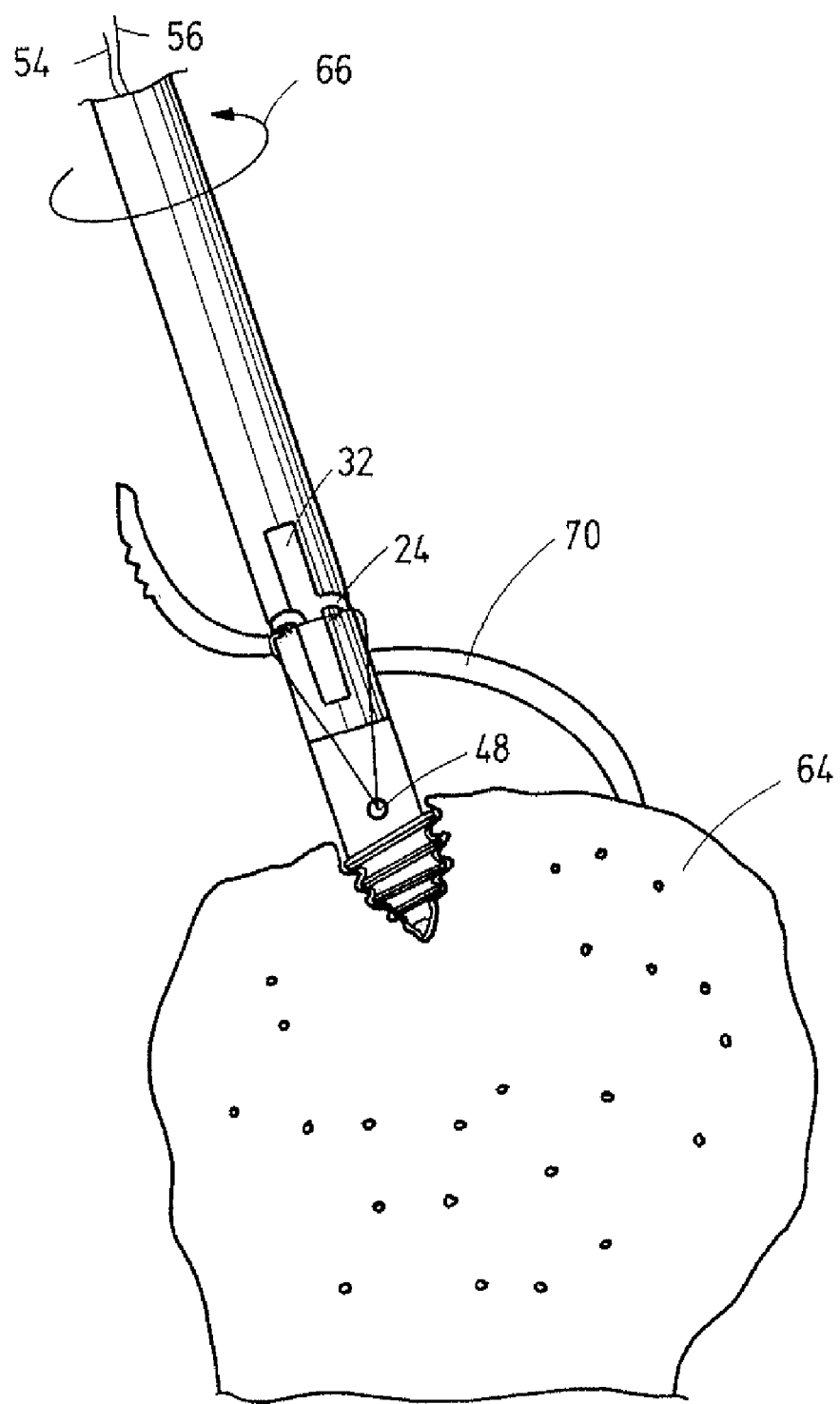
FIG. 6 shows a situation during introduction of the anchor element into a shoulder bone with the device according to the invention, where the assembly shown in FIG. 5 can be seen.

To introduce the anchor element 40 into a bone, the assembly from FIG. 4 or 5 is driven into a shoulder bone 64, for example. To do so, the assembly is rotated, as indicated by an arrow 66 in FIG. 6, such that it is screwed into the shoulder bone 64, this procedure being assisted by the thread 43.

Figure 7:
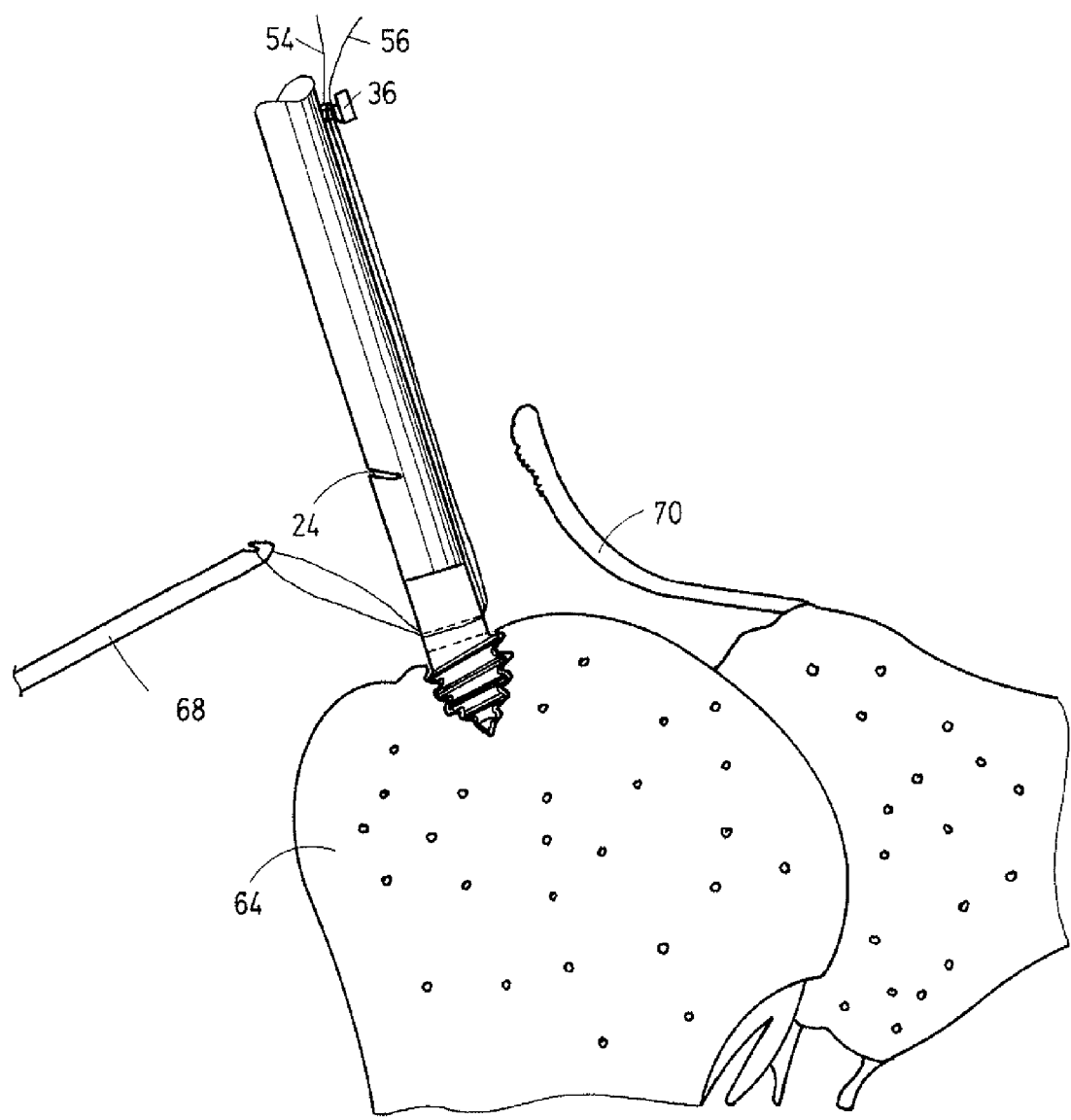
FIG. 7 shows a view comparable to the view in FIG. 6, but turned through 90°, the loop of the thread threaded through the anchor element being gripped by an instrument.

After the anchor element 40 has been turned completely into the shoulder bone 64, the thread portion 62 of the loop 52 inserted in the cutting 24 is gripped by an instrument 68, as is shown schematically in FIG. 7. The instrument 68 can preferably have a hook-shaped distal end, which can be guided into the recess 32 of the device 10.

After the thread portion 62 has been captured by the instrument 68, the thread ends 54, 56 are released from the peg 36, and the instrument 68 is withdrawn with the loop 52 from the device.

A tendon 70, which has been torn from the shoulder bone 64, can then be fixed back on the shoulder bone 64 with the thread ends 54, 56 and the loop 52.

What is claimed is:

1. A device for introducing an anchor element, in which a thread is engaged, into a bone, in order to fix a tissue that is detached from said bone, wherein a loop of said thread extends laterally from said anchor element, said device comprising:

an elongate body having a distal end which can be inserted into said anchor element in a rotationally locked manner, a distal end portion of said elongate body having at least one cutting having inserted said loop laterally protruding from said anchor element, said cutting extending around a circumference of said body, and being designed in such a way that said loop, when inserted into said cutting, is prevented from falling laterally away from said elongate body, and wherein said elongate body has a longitudinally extending recess in an area of said cutting, said recess intersecting and crossing said cutting in a way that a thread portion of said loop inserted in said cutting lies free and said recess being designed as an opening extending right through said elongate body in a direction perpendicular to a circumferential extension of said thread portion inserted into said cutting, such that said loop inserted into said cutting can be gripped from the outside, said thread portion which lies free crosses a width of said recess perpendicular to a longitudinal axis of said elongate body when said loop is drawn taut in said cutting.

2. The device of claim 1, wherein said cutting is designed as an incision extending transversely with respect to a longitudinal axis of said elongate body.

3. The device of claim 1, wherein said cutting, seen from proximal to distal, extends with an inclination in the distal direction.

4. The device of claim 3, wherein said cutting extends with an inclination in the range of 30° to approximately 90°.

5. The device of claim 4, wherein said cutting extends with an inclination of 45°.

6. The device of claim 1, wherein said cutting extends around part of a circumference of said elongate body.

7. The device of claim 6, wherein said cutting extends around half of the circumference of said body.

8. The device of claim 1, wherein said cutting, seen in a radial direction of said elongate body, has a depth that corresponds up to half the diameter of said elongate body.

9. The device of claim 1, wherein said cutting is designed as a slit.

10. The device of claim 1, wherein said recess intersects said cutting centrally.

11. The device of claim 1, wherein said recess has a second opening, the recess extending between the opening and the second opening, wherein the opening and second opening are on either side of said elongate body.

12. A device for introducing an anchor element, in which a thread is engaged, into a bone, in order to fix a tissue that is detached from said bone, wherein a loop of said thread extends laterally from said anchor element, said device comprising:

an elongate body having a distal end which can be inserted into said anchor element in a rotationally locked manner, at least one cutting, the at least one cutting located at the distal end of the elongate body, the at least one cutting having an incision extending transversely with respect to the longitudinal axis of the elongate body, and a longitudinally extending recess, the longitudinally extending recess located in an area of said cutting, said recess being designed as an opening extending right through said elongate body and intersecting and crossing said at least one cutting, wherein the at least one cutting accepts the loop laterally protruding from said anchor element, said cutting being designed in such a way that said loop, when inserted into said cutting, is prevented from falling laterally away from said elongate body, and when the free ends of the thread are drawn taught the loop placed in the incision slides radially, and wherein said recess and said cutting intersect in a way that a thread portion of said loop inserted in said cutting lies free and such that said loop inserted into said cutting can be gripped from the outside, said thread portion which lies free crosses a width of said recess perpendicular to a longitudinal axis of said elongate body when said loop is drawn taut in said cutting.

13. A device for introducing an anchor element, in which a thread is engaged, into a bone, in order to fix a tissue that is detached from said bone, wherein a loop of said thread extends laterally from said anchor element, said device comprising:

an elongate body having a distal end which can be inserted into said anchor element in a rotationally locked manner, a distal end portion of said elongate body having at least one cutting having inserted said loop laterally protruding from said anchor element, said cutting extending around a circumference of said body, and being designed in such a way that said loop, when inserted into said cutting, is prevented from falling laterally away from said elongate body, and wherein said elongate body has a longitudinally extending recess in an area of said cutting, said recess intersecting and extending proximally and distally across said cutting and through said elongate body in a way that a thread portion of said loop inserted in said cutting lies free and said recess being designed as an opening extending right through said elongate body in a direction perpendicular to a circumferential extension of said thread portion inserted into said cutting, such that said loop inserted into said cutting can be gripped from the outside, said thread portion which lies free crosses a width of said recess perpendicular to a longitudinal axis of said elongate body when said loop is drawn taut in said cutting.

* * * * *